(12) United States Patent
Bender et al.

(10) Patent No.: US 9,889,317 B2
(45) Date of Patent: Feb. 13, 2018

(54) SYSTEM AND METHOD FOR AUTOMATED RADIATION TREATMENT PLANNING USING PHYSICAL OBJECTIVES

(71) Applicant: Wisconsin Alumni Research Foundation, Madison, WI (US)

(72) Inventors: Edward T. Bender, Madison, WI (US); Jacob Hoberg, Austin, TX (US)

(73) Assignee: Wisconsin Alumni Research Foundation, Madison, WI (US)

( * ) Notice: Subject to any disclaimer, the term of this patent is extended or adjusted under 35 U.S.C. 154(b) by 681 days.

(21) Appl. No.: 14/471,857

(22) Filed: Aug. 28, 2014

(65) Prior Publication Data

US 2016/0059037 A1    Mar. 3, 2016

(51) Int. Cl.
*A61N 5/00* (2006.01)
*A61N 5/10* (2006.01)

(52) U.S. Cl.
CPC .................. *A61N 5/1031* (2013.01)

(58) Field of Classification Search
CPC .... A61N 5/103; A61N 5/1039; A61N 5/1045; A61N 2005/1041; A61N 2005/1074
USPC .......................................................... 600/1–8
See application file for complete search history.

*Primary Examiner* — John Lacyk
(74) *Attorney, Agent, or Firm* — Quarles & Brady LLP

(57) ABSTRACT

Systems and methods for generating a radiation treatment plan using inverse planning objectives that are automatically determined based on patient data and the physical capabilities of the radiation treatment system are provided. In particular, the planned target volumes and organ-at-risk (OAR) volumes are used to automatically partition the OAR volumes into one or more avoidance volumes, for which particular inverse planning objectives are established based on the physical capabilities of the treatment system. As an example, an inverse planning objective may include establishing a particular dose gradient over one or more avoidance volumes. Because such inverse planning objectives are based on conditions and constraints of the treatment system physics, rather than a desired percentage of the prescribed dose, they may be referred to as "physical objectives."

17 Claims, 6 Drawing Sheets

SYSTEM AND METHOD FOR AUTOMATED RADIATION TREATMENT PLANNING USING PHYSICAL OBJECTIVES

BACKGROUND OF THE INVENTION

The field of the invention is systems and methods for radiation treatment planning. More particularly, the invention relates to systems and methods for automated radiation treatment planning using physical objectives that are based on the physical properties of a radiation therapy system.

In radiation treatment planning it is desirable to compute optimal treatment plans that deliver an optimized dose to the patient. In these plans, varying levels of radiation are delivered using beam apertures from various angles around the tumor to deliver the highest dose to the tumor while minimizing dose to non-tumor tissues. Typically, treatment planning is done on a case-by-case basis by medical physicists, medical dosimetrists, or both. Treatment plans are based on a dose prescribed by a physician and are computed using radiation treatment planning software.

The process of treatment planning is iterative, in that the medical physicist or medical dosimetrist starts with a "guess" and enters a number of parameters into the system that he believes will be close to providing the prescribed dose to the target tissue while sparing other tissue from radiation. There are quite a number of parameters that can be modified, so the iterative process can many times be quite time consuming.

Given the importance of plan quality in terms of a given patient's probability of disease control and severe toxicities, there remains a need to provide a standardized methodology for how to consistently achieve a high quality radiation treatment plan. Currently, in clinical practice, a trial and error process is used to define the inverse planning objectives that yield a clinically acceptable plan. Though the treatment planning goals are simple (e.g., achieving conformal target coverage and a low dose to critical structures), achieving all of these goals simultaneously is difficult. Because of the technical challenge in developing a good treatment plan in a clinical setting, neither the physician, dosimetrist, nor medical physicist may be aware of what the best achievable plan quality is for a given patient. Accordingly, the quality of a treatment plan used clinically is both a reflection of the technology used and the quality of the inverse planning objectives chosen during plan optimization.

It would therefore be desirable to provide a method for radiation treatment planning that is capable of achieving a consistently high plan quality across different patients and therapy systems.

SUMMARY OF THE INVENTION

The present invention overcomes the aforementioned drawbacks by providing a method for producing a radiation treatment plan for a patient, in which at least one image of the patient is provided. A target volume in the patient is identified based on the at least one image of the patient, where this target volume includes a volume bounded by an outer boundary. An organ at risk ("OAR") volume is also identified based on the at least one image of the patient. A plurality of avoidance volumes are then generated based on the identified OAR volume. A target objective is determined based on the identified treatment volume, where the target objective indicates a desired dose distribution in the target volume. A physical objective is also determined for each of the plurality of avoidance volumes. Each physical objective is based a physical capability of a radiation treatment system and indicates a desired dose gradient across the plurality of avoidance volumes. A radiation treatment plan is then generated by a radiation treatment planning system, to which the target objective and physical objectives are provided. The radiation treatment planning system is programmed to generate an optimized radiation treatment plan by optimizing an objective function based at least in part on the target objective and physical objectives.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for generating a radiation treatment plan using inverse planning objectives that are automatically determined based on patient data, which may include planning target volumes ("PTVs") and regions containing identified organs at risk ("OARs"). In particular, the PTVs and OARs are used to automatically partition the OAR volumes into one or more avoidance volumes, for which particular inverse planning objectives will be established based on the physical capabilities and characteristics of the treatment system. As an example, an inverse planning objective may include establishing a particular dose gradient over a particular avoidance volume. Because such inverse planning objectives are based on conditions and constraints of the treatment system physics, rather than a desired percentage of the prescribed dose, they may be referred to as "physical objectives."

Figure 1:
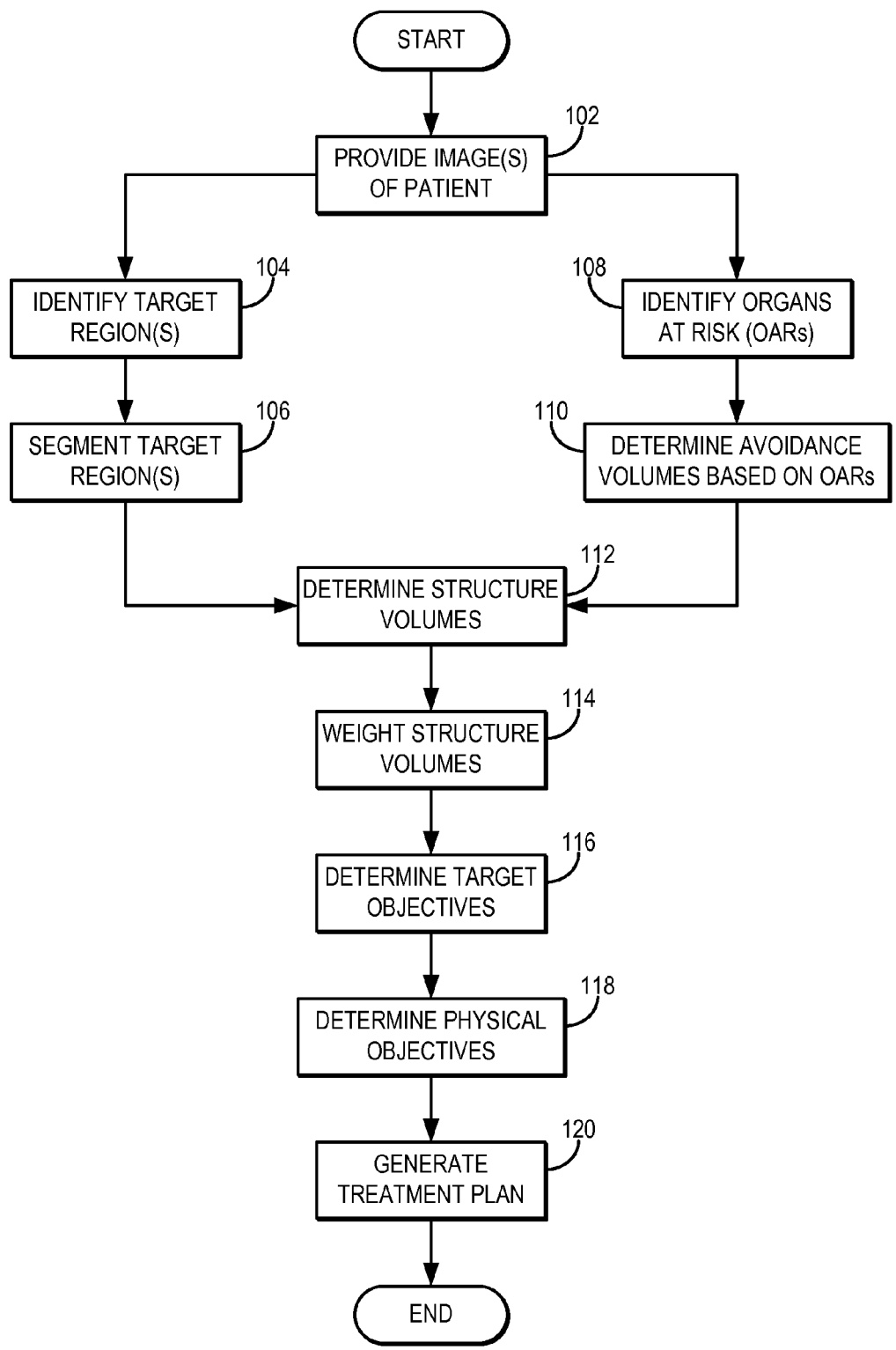
FIG. 1 is a flowchart setting forth the steps of an example method for generating a radiation treatment plan using physical objectives that are automatically determined based on patient data.

Referring now to FIG. 1, a flowchart is illustrated as setting forth the steps of an example method for generating a radiation treatment plan using physical objectives that are automatically determined based on patient data. The method includes providing one or more images of the patient for whom the treatment plan is to be generated, as indicated at step 102.

Based on the one or more images of the patient, one or more target regions, such as planning target volumes ("PTVs"), are identified, as indicated at step 104. As an example, the one or more target regions can be manually drawn by a user, such as a medical physicist or clinician. As another example, the one or more target regions can be automatically or semi-automatically identified, such as by using image segmentation methods.

Figure 2A:
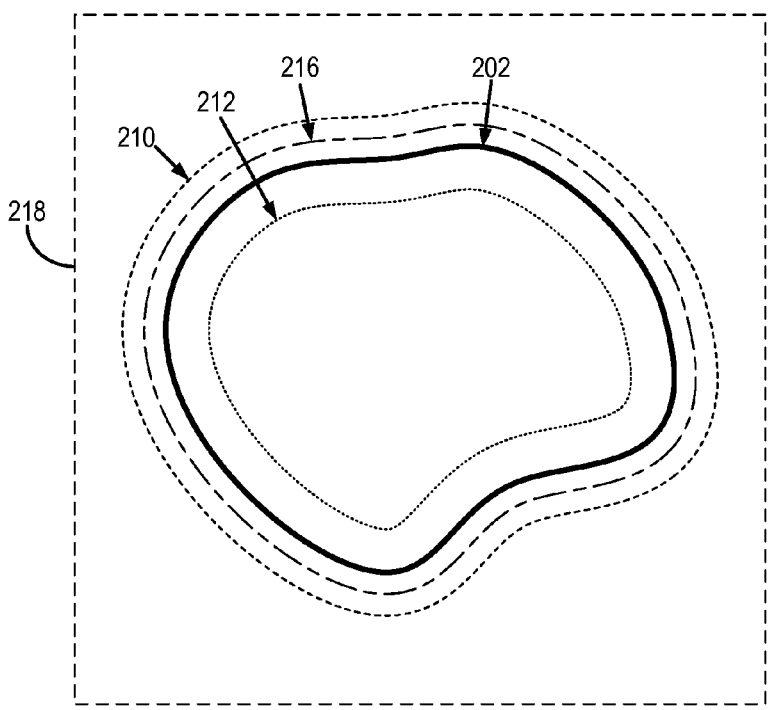
FIG. 2A illustrates an example target volume and multiple different margins based on the target volume boundary that can be used to define different target structures.
Figure 2B:
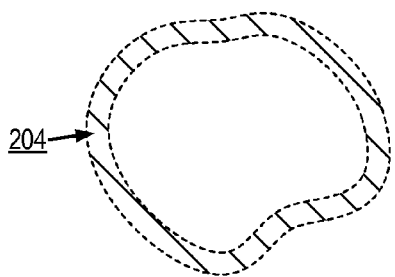
FIG. 2B is an example illustrating an exterior margin volume target structure determined based on an exterior margin and the target volume of FIG. 2A.
Figure 2C:
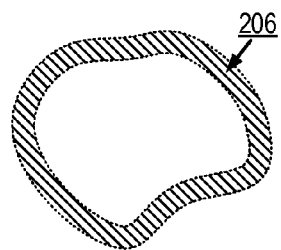
FIG. 2C is an example illustrating an interior margin volume target structure determined based on an interior margin and the target volume of FIG. 2A.
Figure 2D:
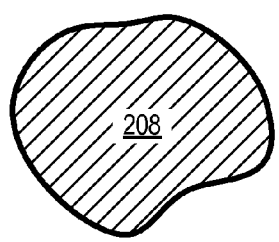
FIG. 2D is an example illustrating a target volume structure determined based on the target volume of FIG. 2A.
Figure 2E:
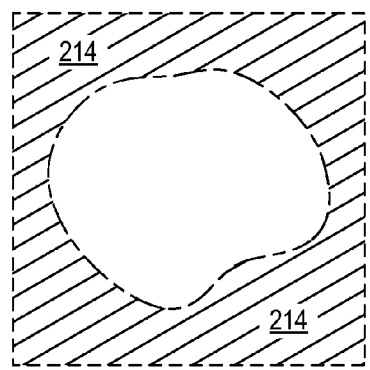
FIG. 2E is an example illustrating a background target structure determined based on a total image volume and the target volume of FIG. 2A.

Multiple target structures are then formed based on the one or more identified target regions, as indicated at step 106. For instance, as illustrated in FIGS. 2A-2E, a given target region 202 can be the basis for three different target structures: an exterior margin volume 204 (FIG. 2B), an interior margin volume 206 (FIG. 2C), and a target volume 208 (FIG. 2D). In this example, the target volume 208 is the volume of the identified target region 202. The exterior margin volume 204 can be generated by dilating the target volume 208 and then subtracting the target volume 208 from the dilated volume 210. As a non-limiting example, the target volume 208 can be dilated by 4 mm, such as by using a 4 mm structuring element.

The interior margin volume 206 can be generated by eroding the target volume 208 and then subtracting the eroded volume 212 from the target volume 208. As a non-limiting example, the target volume 208 can be eroded by 4 mm, such as by using a 4 mm structuring element.

A background target structure 214 (FIG. 2E) can also be generated. The background target structure 214 can be generated by dilating the target volume 208 and then subtracting the dilated volume 216 from the total image volume 218, or a subvolume thereof that contains all or part of the target volume 208. As a non-limiting example, the target volume 208 can be dilated by 2 cm, such as by using a 2 cm structuring element.

Referring again to FIG. 1, in addition to forming target structures, one or more avoidance structures are also formed. This process includes identifying one or more organs at risk ("OARs") in the one or more images of the patient, as indicated at step 108. As an example, the one or more OARs can be manually drawn by a user, such as a medical physicist or clinician. As another example, the one or more OARs can be automatically or semi-automatically identified, such as by using image segmentation methods.

Figure 3A:
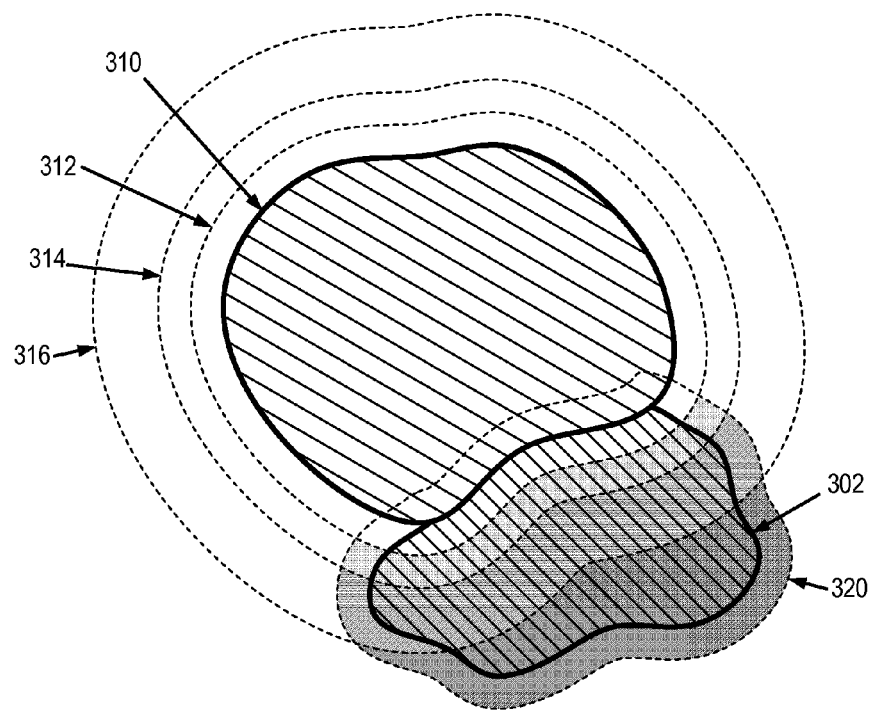
FIG. 3A illustrates an example of an organ-at-risk ("OAR") volume and avoidance volumes generated based on the OAR volume and multiple different boundaries located at different distances from the surface of the OAR volume'
Figure 3B:
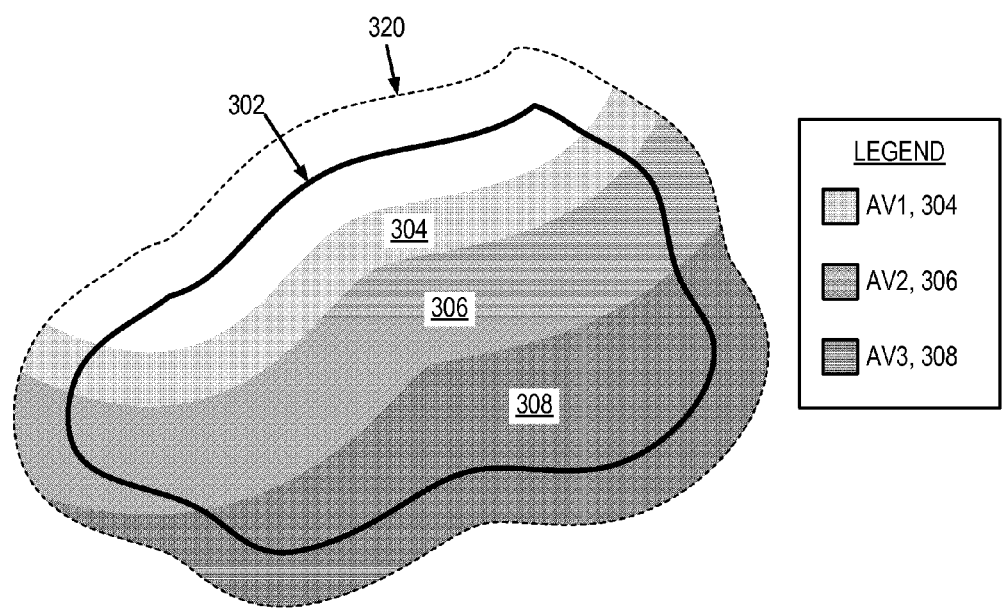
FIG. 3B is an example of different avoidance volumes that are determined based on the OAR illustrated in FIG. 3A.
Figure 4A:
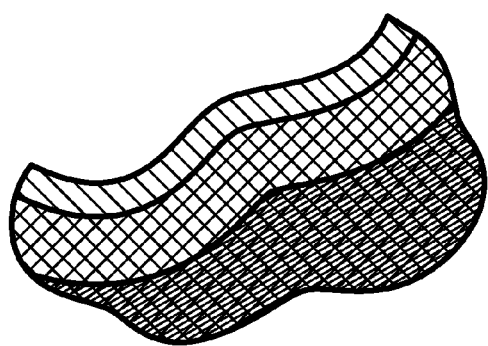
FIGS. 4A-4D illustrate examples of overlapping avoidance volumes.
Figure 4B:
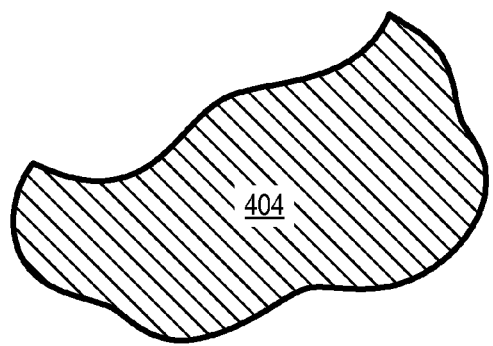
Figure 4C:
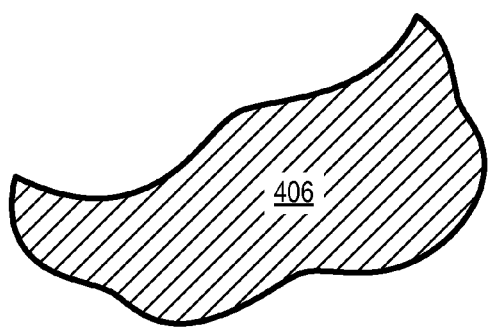
Figure 4D:
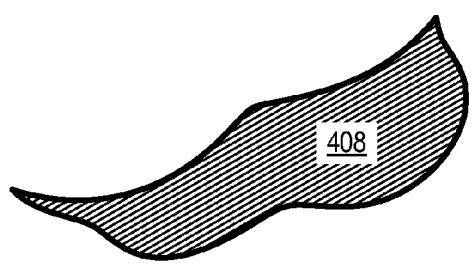
Figure 5A:
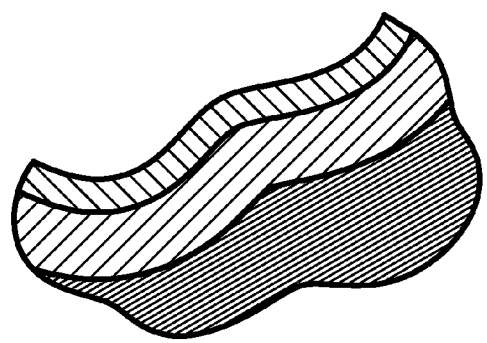
FIGS. 5A-5D illustrate examples of non-overlapping avoidance volumes.
Figure 5B:
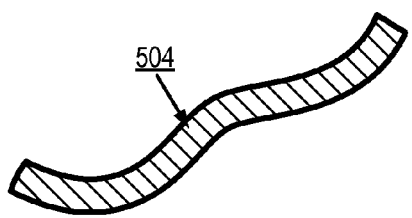
Figure 5C:
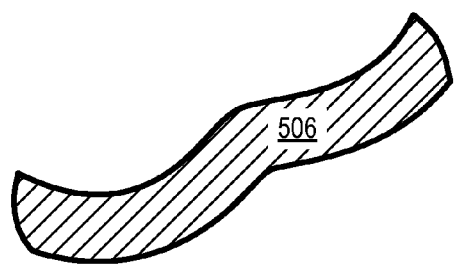
Figure 5D:
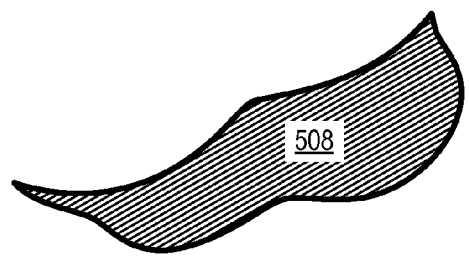

One or more avoidance volumes are then formed based on the one or more identified OARs, as indicated at step 110. For instance, as illustrated in FIGS. 3A and 3B, a given OAR 302 can be the basis for three different avoidance volumes: AV1 304, AV2 306, and AV3 308.

In general, avoidance volumes are defined based on a distance from the outer surface of the target volume 310. For instance, one or more avoidance boundaries can be defined at specified distances from the outer surface of the target volume 310, and the avoidance volumes can be defined based on the volume of the OAR 302 existing beyond the respective avoidance boundary. In some embodiments, the avoidance volumes are also defined to encompass a margin extended around the OAR 302, as will be described below.

As a non-limiting example, three avoidance boundaries can be defined, as illustrated in FIG. 3A. In this example, the first avoidance boundary 312 is defined as the contour of the target volume 310 dilated by 0.5 cm; the second avoidance boundary 314 is defined as the contour of the target volume 310 dilated by 1 cm; and the third avoidance boundary 316 is defined as the contour of the target volume 310 dilated by 2 cm. The OAR volume 302 can similarly be dilated out to an extended OAR boundary 318, thereby defining an "extended" OAR volume. The avoidance volumes can the be defined based on the avoidance boundaries (312, 314, 316) and the extended OAR volume. For instance, the avoidance volumes can be defined using set theory operations, such as unions, intersections, and complements.

In some embodiments, the avoidance volumes are overlapping, whether in whole or in part. For example, as illustrated in FIGS. 4A-4D, AV1 404 can be defined as the extended volume of the OAR extending beyond the first avoidance boundary. Likewise, AV2 406 can be defined as the extended volume of the OAR extending beyond the second avoidance boundary, and AV3 408 can be defined as the extended volume of the OAR extending beyond the third avoidance boundary. With these definitions, AV2 406 and AV3 408 are subsets of AV1 404 since their volumes are wholly contained within AV1 404, and AV3 408 is similarly a subset of AV2 406.

Stated another way, AV1 404 is the relative complement, or set difference, of the volume defined by the first avoidance boundary and the volume defined by the extended OAR boundary; AV2 406 is the relative complement, or set difference, of the volume defined by the second avoidance boundary and the volume defined by the extended OAR boundary; and AV3 408 is the relative complement, or set difference, of the volume defined by the third avoidance boundary and the volume defined by the extended OAR boundary.

In some other embodiments, the avoidance volumes are non-overlapping. For example, as illustrated in FIGS. 5A-5D, AV1 504 can be defined as the volume of the OAR bounded by the first avoidance boundary and the second avoidance boundary. In this example, AV2 506 can then be defined as the volume of the OAR bounded by the second avoidance boundary and the third avoidance boundary The most distal avoidance volume, AV3 508, is then defined as the volume of the OAR extending beyond the third avoidance boundary.

It will be appreciated that in other embodiments some of the avoidance volumes may be overlapping and some of the avoidance volumes may be non-overlapping, such that there is a combination of overlapping and non-overlapping avoidance volumes.

Referring again to FIG. 1, the method proceeds by determining the structure volumes for which physical objectives should be established, as indicated at step 112. In general, this step includes selecting the already computed target structures and by selecting the computed avoidance volumes as avoidance structures. A structure volume can thus refer to either a target structure volume or an avoidance structure volume. The structure volumes can then be assigned different weights, as indicated at step 114. For instance, each structure volume can be assigned a weight according to, $$SV'_i = w_i \left( \frac{SV_i}{V_{PTV}} \right); \qquad (1)$$

where $SV'_i$ is the $i^{th}$ weighted structure volume, $SV_i$ is the $i^{th}$ structure volume, $w_i$ is the weight value applied to the $i^{th}$ structure volume, and $V_{PTV}$ is the volume of the planned target volume structure, as described above. This weighted structure volume can be used as a multiplicative factor for the inverse planning objectives described below. For example, the weighted structure volume can be used as a multiplicative factor for weighting the inverse planning objective defined by Eqn. (2).

Target objectives are then determined for each weighted target structure volume, as indicated at step 116. The target objectives are determined based on the weighted target structure volumes and on a prescribed dose that is provided by a user, such as a medical physicist or clinician.

Physical objectives are also determined for the weighted structure volumes, as indicated at step 118. Like the target objectives, the physical objectives are based in part on a prescribed dose provided by a user, such as a medical physicist or clinician. Preferably, the physical objectives for the avoidance volumes are based on the physical capabilities of the treatment system.

In general, the physical objectives are designed to achieve a treatment plan that is optimal based on the physical parameters and capabilities of a particular radiation treatment system. This approach is contrary to traditional treatment planning, which is typically based on trying to achieve a dose-volume histogram ("DVH") that fails to convey the same spatial information attainable with the physical objectives. For instance, the physical objectives for the avoidance volumes can be based on achieving a specified dose gradient in the avoidance volume, where the dose gradient is controlled by the physical capabilities of the treatment system that will be used.

As an example, a photon-based radiation treatment system may be able to achieve a dose gradient of 10 percent per millimeter, whereas a proton-based treatment system may be able to achieve a sharper dose gradient. The dose gradients can also be based on the anatomy being treated. For instance, a dose gradient of 7 percent per millimeter may be acceptable for treating the bladder, but a sharper dose gradient of 10 percent per millimeter may be preferable for treating the rectum where there are stricter requirements on normal tissue sparing.

The dose gradients are established with respect to the weighted structure volumes. As an example, the dose gradient is established with respect to the avoidance volumes determined above, such that a physical objective describes achieving a particular dose gradient over the different avoidance volumes. For instance, the physical objective may describe achieving a 10 percent dose gradient per millimeter based on the physical dimensions and arrangement of the avoidance volumes determined above. In some instances, the physical objective may include a cutoff value, after which the objective doses will no longer decrease with increasing distance from the PTV. For example, when a particular dose gradient is unable to be maintained across the avoidance volumes (e.g., where 10 percent/mm reaches zero dose at 1 cm) then a cutoff value (e.g., 20 percent of the prescription dose) can be used such that the objective doses don't decrease below the cutoff value with increasing distance from the PTV.

A radiation treatment plan is then generated based on the target objectives and the physical objectives, as indicated at step 120. For instance, an inverse planning algorithm can be used to generate the treatment plan based on the target and physical objectives. As an example, the inverse planning algorithm may include minimizing the sum of the target and physical objectives, $$f(x) = \sum_{m=1}^{M} T_m + \sum_{n=1}^{N} P_n; \qquad (2)$$

where x is the set of parameters to optimize; $T_m$ is a target objective with m=1, ..., M; and $P_n$ is a physical objective with n=1, ..., N. In some embodiments, additional constraints can be added to this optimization task. For example, a dose uniformity constraint can be added to minimize dose variation in one or more of the structure volumes.

It is an advantage of the present invention that the treatment plans generated using the methods described above are inherently patient-specific because they are computed based on structure volumes identified for the particular patient. This feature of the radiation treatment planning process enables a high quality plan to be developed because the treatment plan is based on the best possible physical outcome that a given treatment system can achieve for a particular patient.

Figure 6:
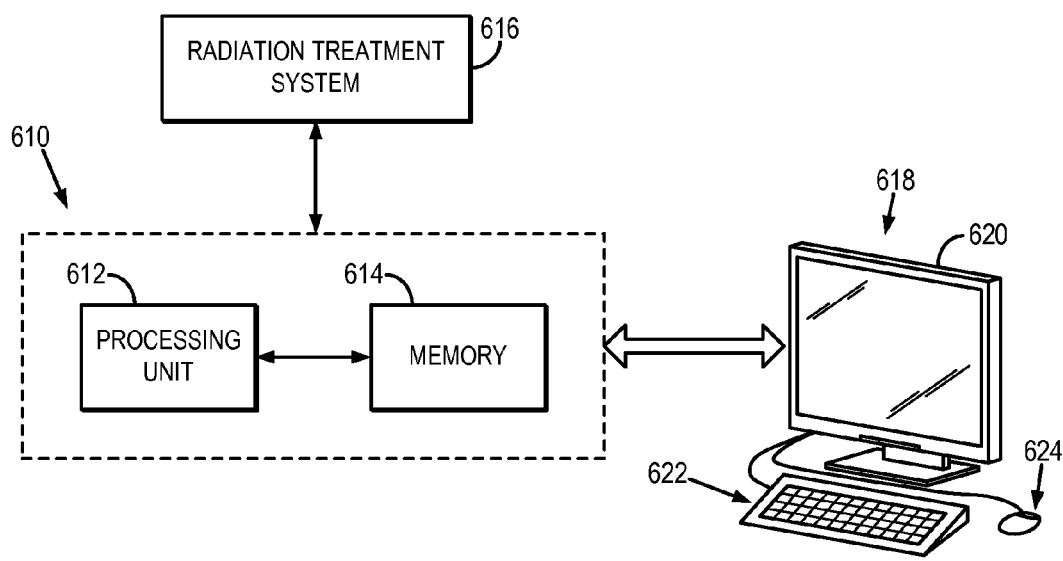
FIG. 6 is a block diagram of an example radiation treatment planning system that can implement the methods of the present invention.

The methods described above can be implemented using a suitable radiation treatment planning system. Referring now to FIG. 6, an example of such a radiation treatment planning system 610 is illustrated. The radiation treatment planning system 610 is preferably in communication with one or more radiation treatment systems 612, which may include any suitable radiation treatment system, including intensity-modulated radiation therapy ("IMRT") systems such as intensity-modulated arc therapy ("IMAT") and volumetric modulated arc therapy ("VMAT") systems. In such systems, the treatment beam can be composed of photons, neutrons, electrons, protons, heavy charged particles, or the like.

The radiation treatment planning system 610 generally includes a memory 614 that is operably coupled to a processor unit 616. As an example, the processor unit 616 can be a commercially available computer processor, such as those described above. The processor unit is configured to carry out one or more of the steps of the methods described above.

As an example, the memory 614 can include a plurality of memory elements, or can include a single memory element. In general, the memory 614 is configured to store information regarding patient data, including images of the patient, treatment volumes, organs at risk, prescribed dose information, inverse planning objectives, and so on.

Preferably, the radiation treatment planning system 610 includes, or is otherwise in communication with, a user interface 618. As an example, the user interface 618 provides information to a user, such as a medical physicist. For example, the user interface 618 can include a display 620 and one or more input devices, such as a keyboard 622 and mouse 624.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a radiation treatment plan for a patient using a radiation treatment planning system, the steps of the method comprising:
   (a) providing at least one image of a patient to a radiation treatment planning system;
   (b) identifying with the radiation treatment planning system, a target volume in the patient based on the at least one image of the patient, the target volume comprising a volume bounded by an outer boundary;
   (c) identifying with the radiation treatment planning system, an organ at risk (OAR) volume based on the at least one image of the patient;
   (d) generating with the radiation treatment planning system, a plurality of avoidance volumes based on the identified OAR volume;
   (e) determining with the radiation treatment planning system, a target objective based on the identified treatment volume, the target objective indicating a desired dose distribution in the target volume;
   (f) determining with the radiation treatment planning system, a physical objective for each of the plurality of avoidance volumes, each physical objective being based a physical capability of a radiation treatment system and indicating a desired dose gradient across the plurality of avoidance volumes; and
   (g) generating with the radiation treatment planning system, a radiation treatment plan by providing the target objective and physical objectives to the radiation treatment planning system, wherein with the radiation treatment planning system is programmed to generate an optimized radiation treatment plan by optimizing an objective function based at least in part on the target objective and physical objectives.

2. The method as recited in claim 1, further comprising generating with the radiation treatment planning system, a plurality of target structure volumes based on the identified target volume; and wherein step (e) includes determining with the radiation treatment planning system, a different target objective for each target structure volumes and step (g) includes providing the different target objectives to the radiation treatment planning system.

3. The method as recited in claim 2, wherein the plurality of target structure volumes comprise an exterior margin target volume, an interior margin target volume, and the target volume; and wherein:
   the exterior margin target volume comprises a volume bounded by the outer boundary of the target volume and an exterior margin defined with the radiation treatment planning system by a surface located outward from and enclosing the outer boundary of the target volume; and
   the interior margin target volume comprises a volume bounded by the outer boundary of the target volume and an interior margin defined with the radiation treatment planning system by a surface located inward from and enclosed within the outer boundary of the target volume.

4. The method as recited in claim 3, wherein the exterior margin is defined with the radiation treatment planning system by dilating the outer boundary of the target volume.

5. The method as recited in claim 3, wherein the interior margin is defined with the radiation treatment planning system by eroding the outer boundary of the target volume.

6. The method as recited in claim 3, wherein the plurality of target structure volumes further comprise a background volume defined with the radiation treatment planning system as a set difference of the target volume from a field-of-view containing the target volume.

7. The method as recited in claim 6, wherein the outer boundary of the target volume is dilated by the radiation treatment planning system before performing the set difference.

8. The method as recited in claim 3, wherein step (e) includes weighting each target structure volume with the radiation treatment planning system based on a weight value.

9. The method as recited in claim 8, wherein each target structure volume is weighted in step (c) with the radiation treatment planning system according to, $$SV' = w \cdot \left(\frac{SV}{V_{PTV}}\right)$$

wherein SV' is the weighted target structure volume, SV is the target structure volume, w is the weight value, and $V_{PTV}$ is a volume of the target volume.

10. The method as recited in claim 1, wherein each avoidance volume is generated with the radiation treatment planning system based on a subvolume of the OAR volume and a distance from the outer boundary of the target volume.

11. The method as recited in claim 10, wherein step (d) includes defining a plurality of different avoidance boundaries, each avoidance boundary defined with the radiation treatment planning system by a surface located at a different distance from the outer boundary of the target volume.

12. The method as recited in claim 11, wherein each avoidance volume is generated with the radiation treatment planning system as a set difference of a volume defined by one of the plurality of different avoidance boundaries from the OAR volume.

13. The method as recited in claim 11, wherein each avoidance volume is defined with the radiation treatment planning system as a subvolume of the OAR volume bounded by two different avoidance boundaries.

14. The method as recited in claim 1, wherein step (f) includes assigning a different maximum allowable dose to each avoidance volume with the radiation treatment planning system, such that the desired dose gradient is defined across the avoidance volumes.

15. The method as recited in claim 1, wherein the desired dose gradient is set by with the radiation treatment planning system as less than about 10 percent per millimeter.

16. The method as recited in claim 1, wherein the desired dose gradient across the plurality of avoidance volumes is set by with the radiation treatment planning system based on anatomy contained in the plurality of avoidance volumes.

17. The method as recited in claim 1, wherein step (g) includes generating the objective function with the radiation treatment planning system as a sum of the target objective and the physical objectives.

* * * * *